United States Patent [19]

Giovannini

[11] 3,990,150
[45] Nov. 9, 1976

[54] DENTAL PROSTHESIS ATTACHMENT
[75] Inventor: Guglielmo Giovannini, Bologne, Italy
[73] Assignee: Metaux Precieux SA, Switzerland
[22] Filed: June 13, 1975
[21] Appl. No.: 586,749

[30] Foreign Application Priority Data
June 17, 1974 Switzerland.......................... 8282/74

[52] U.S. Cl. ..................................................... 32/5
[51] Int. Cl.² ......................................... A61C 13/22
[58] Field of Search.................................. 32/5, 6, 7

[56] References Cited
FOREIGN PATENTS OR APPLICATIONS
188,440  1/1957  Germany .................................. 32/5

541,013  3/1956  Italy ........................................... 32/5

Primary Examiner—Louis G. Mancene
Assistant Examiner—Jack Q. Lever
Attorney, Agent, or Firm—Stevens, Davis, Miller & Mosher

[57]  ABSTRACT

A dental prosthesis made of two elements. A first fixed slide portion has a profile into which is adapted to be inserted two balls which are connected to the second detachable body portion. One of the balls is rigidly secured to the body portion while the second ball is connected to the body portion by a shock-absorber device.

10 Claims, 7 Drawing Figures

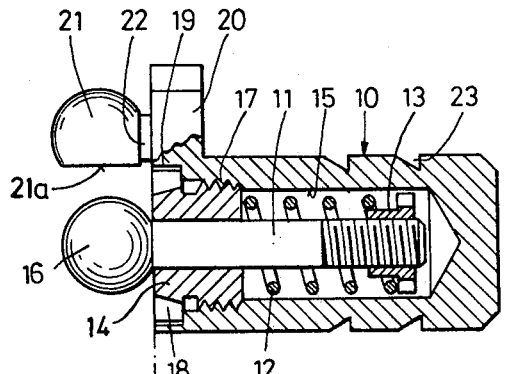
FIG. 2
FIG. 1
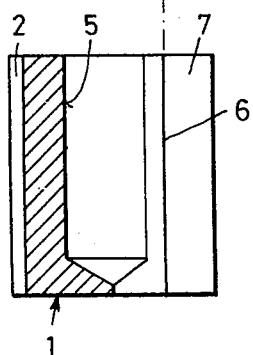
FIG. 3
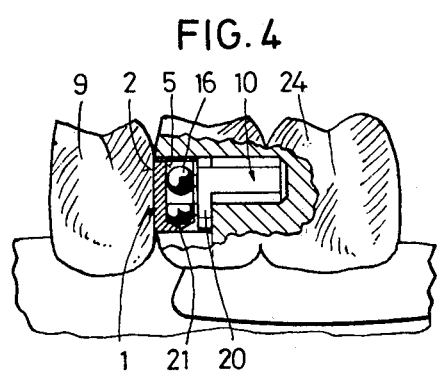
FIG. 4
FIG. 5
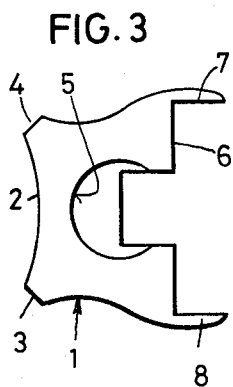
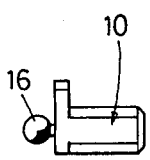
FIG. 6
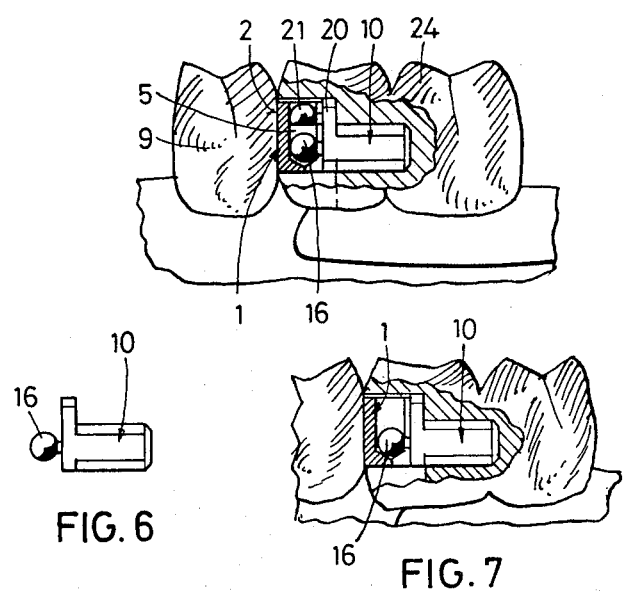
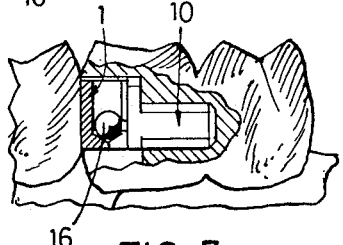
FIG. 7

DENTAL PROSTHESIS ATTACHMENT

This invention relates to a dental prosthesis attachment comprising a fixed portion and a detachable portion, the fixed portion of which comprises a slide.

In the art of prosthodontics, "attachment" is the name given to a device which enables a prosthesis to be connected to the natural teeth in such a way as to be attached to the natural teeth as to a pillar. The device comprises two portions. One of them is rigidly secured, e.g., to a crown integral with a natural tooth, while the other is secured, generally by anchoring, but also by soldering or other means, to the prosthesis.

Attachments for dental prostheses must meet requirements which vary according to the particular application and which are sometimes contradictory. In the case of unilateral prostheses, the system of attachment must be rigid enough to ensure the fastening of the prosthesis by itself. In certain cases, however, it is desirable to prevent the possibility of undue stress being transmitted from the prosthesis to the natural tooth either when the prosthesis is being fitted or when it is in use. In the case of attachments used for holding bilateral prostheses in place, it is advantageous to use devices having a certain elasticity in order to enable easier adaptation of the detachable portions of the attachments to each of the fixed portions after these fixed portions have been secured to the natural teeth.

So-called "shock-absorber" attachment systems which ensure such elasticity are already known. They comprise a socket-shaped body, intended to be secured to the prosthesis, and a pin, threaded at one end, on which are mounted an adjustable nut, a spring, and a threaded coupling screwed into the body. The spring presses on the threaded coupling and on the nut. At the non-threaded end of the pin is a head, in the form of a ball, for example, which engages in the fixed portion of the attachment, the latter frequently being in the nature of a slide. The advantage of these attachment devices is that they can be adjusted at will. It suffices to screw the nut back or forth on the threaded pin to cause the preloading of the spring to vary.

Also known are hinged attachment devices, likewise equipped with a return spring, in which the only movement that the prosthesis can effect with respect to the tooth in place is a distal axial rotation.

The various types of known attachments are generally produced in several variations according to whether they are intended for unilateral or bilaterial prostheses and whether they are equipped with a protective device or not.

It is the object of this invention to provide a dental prosthesis attachment having virtually universal possibilities of use. More particularly, the invention aims at providing an attachment capable of being used as either a rigid attachment or a shock-absorber attachment and, especially, of being initially fitted as a rigid attachment and then, when it has been in use for a certain length of time, and after disengagement of the detachable portion, of being modified, then refitted, and thereafter functioning as a shock-absorber attachment.

To this end, in the dental prosthesis attachment according to the present invention, the detachable portion comprises a body equipped with two balls, one of the balls being rigidly secured to the body and the other being connected to the body by a shock-absorber device.

A preferred embodiment of the invention will now be described in detail with reference to the accompanying drawings, in which:

FIG. 1 is a sectional view showing the two portions of the attachment disengaged from one another, FIG. 2 is a front elevation of the detachable portion of the attachment shown in FIG. 1, FIG. 3 is a top plan view of the fixed portion of this attachment, FIGS. 4 and 5 are elevations, partially cut away and on a smaller scale, illustrating the use of the attachment shown in FIG. 1 as a rigid attachment (FIG. 5), on the one hand, and as a hinged attachment (FIG. 4), on the other hand, FIG. 6 is a side elevation on a still further reduced scale showing the attachment of FIG. 1 after having undergone a modification intended to enable it to be used as a shock-absorber attachment, and FIG. 7 is a view of the latter attachment after having been put in place.

The fixed portion of the attachment shown in the drawing consists of a slide 1. It is a metal part which may be produced by turning and has a curved front surface 2 limited by two parallel chamfers 3 and 4. Surface 2 is intended to be set against an element covering a natural tooth. It may, for example, be soldered to a crown fitted on such a tooth. Chambers 3 and 4 ensure the proper holding of slide 1. On the side of slide 1 facing the prosthesis is a straight groove 5 extending parallel to surface 2 and opening out into a flat support surface 6 limited by two parallel edges 7 and 8. Groove 5 has a keyhole-shaped profile comprising an arcuate portion with an angular span of more than 180° and a slot with parallel sides, opening out into flat surface 6. It may be machined in two operations: a boring operation using a drill-bit engaged in slide 1 parallel to surface 2, without, however, passing all the way through; and a milling operation using a flat milling-cutter which cleaves the material of slide 1 between flat surface 6 and the previously-made bore. Slide 1 will be secured, as may be seen in FIGS. 4 and 5, to a crown affixed to a natural tooth 9, the securing means not being shown in detail in those figures, in such a way that the axis of groove 5 is parallel to the axis of tooth 9 and the bottom of groove 5 is situated toward the gum.

The detachable portion of the attachment described comprises a body 10, containing a housing 15, a threaded shank 11, a spiral spring 12 engaged on shank 11, an adjusting nut 13 which is screwed on the threading of shank 11, and a threaded coupling 14 screwed into the mouth of housing 15 and provided with a hole through which shank 11 passes. As may be seen especially in FIGS. 1 and 2, the amount of tension on spring 12 may be adjusted by tightening nut 13 to a greater or lesser extent. Spring 12 presses on threaded coupling 14, on the one hand, and on nut 13, on the other hand. Via nut 13, it urges shank 11 toward the right, as viewed in FIG. 1, so that a ball 15 formed at the outer end of shank 11 lies against the rim of the axial opening of coupling 14. Coupling 14 is screwed home in a thread 17 of body 10, and its peripheral flange, which is slotted at four points 18 to allow screwing of coupling 14, rests against the bottom of an annular undercut 19 at the mouth of housing 15. Thus the front face of coupling 14 is flush with the front face of body 10. As may be seen in FIG. 1, the front face of body 10 extends upward to form the front face of a lateral flange 20 of body 10. Owing to flange 20, the front face of body 10 appears as a rectangle with the short sides rounded. Projecting from flange 20 is a second ball 21 of the same diameter as ball 16, but having a flat 21a facing ball 16. Ball 21 will be machined in one piece with body 10 and flange 20. Both its diameter and that of ball 16 are fitted to the dimensions of groove 5 so as to be able to engage in groove 5. In particular, ball 21 will be connected to flange 20 by a cylindrical connecting element 22, likewise cut off by a flat and corresponding in length to the mouth of groove 5.

Body 10 will preferably be secured to a dental prosthesis by anchoring in the resin with the aid of grooves 23 machined in the outer surface of the socket-shaped part of body 10.

FIGS. 4 and 5 show two possible ways of mounting the detachable portion of the attachment described here. According to FIG. 4, flange 20 bearing fixed ball 21 points downward, i.e., toward the gum, with respect to the part forming the socket and carrying shank 11 provided with ball 16. The prosthesis, shown diagrammatically as 24, in which body 10 is anchored, is set in place by engaging the detachable portion of the attachment in slide 1, which is secured against tooth 9 acting as a pillar. Fixed ball 21 is engaged in slide 1 first. It comes to rest against the bottom of groove 5, with ball 16 being engaged following it. Body 10, flange 20 of which is fitted in width to the space between edges 7 and 8 of slide 1, cannot undergo any vestibular-lingual rotation. Translatory movements are likewise prevented because fixed ball 21, engaged in groove 5, keeps flange 20 in contact with surface 6 of slide 1. It will be seen that owing to the flexibility of the gum, prosthesis 24 can describe only a hinge movement. The pivot is fixed ball 21, the return is caused by spring 12 mounted on the axis of ball 16.

Under these conditions of use, the attachment makes it possible to keep too strong forces from being transmitted to tooth 9. This possibility is particularly advantageous in the case of bilateral prostheses, in which two attachments such as the one described above are respectively mounted on one and the other of the main parts of the prosthesis. In this case, the prosthesis is fitted in place under the best possible conditions, without transmitting unduly great forces to the teeth acting as pillars. This advantage is also a valid one when the pillar-teeth cannot take rigid anchoring.

If, on the other hand, body 10 is anchored in prosthesis 24 as shown in FIG. 5, i.e., with flange 20 pointing upward or, with respect to the socket, on the side opposite the gum, prosthesis 24 can no longer perform a hinge movement. It is rigidly fixed to tooth 9. Ball 21, integral with flange 20, allows no hinge movement of the prosthesis toward the gum.

However, the attachment described may equally well be used, not as a hinge-type attachment as is shown in FIG. 4, but as a pure shock-absorber attachment. For that purpose, it suffices to mill off fixed ball 21 and its connecting element 22, leaving flange 20, and to mount the attachment as shown in FIG. 5. In this case, spring 12 tends to press the prosthesis against tooth 9. The pivoting movements described above are no longer possible because flange 20 is pressed flat against support surface 6. However, the force of that pressure, which depends upon the tension of spring 12, can be adjusted by means of nut 13. Thus a prosthesis originally fitted so as to be fixed, according to the arrangement of FIG. 5, may, after being in use for several months or several years, be transformed into an elastically attached prosthesis. For that purpose, it suffices to extract the body or bodies 10, to eliminate the balls 21, thus obtaining the attachment shown in FIG. 6, and to refit the detachable portions of the attachments in the position shown in FIG. 7.

Thus the object of the invention, consisting in providing a universal-type attachment which can be used both as a rigid attachment and as a pivoting attachment or as a shock-absorber attachment, has been achieved.

What is claimed is:

1. A dental prosthesis attachment comprising a fixed portion and a detachable portion, said fixed portion comprising a slide, wherein said detachable portion comprises a body equipped with two balls, one said ball being rigidly secured to said body and the other said ball being connected to said body by a shock-absorber device, said slide having a profile adapted to receive both said balls when engaged therein the one behind the other.

2. An attachment according to claim 1, wherein said body is composed of a socket-shaped part containing a housing for said shock-absorber device and of a lateral flange bearing said rigidly-secured ball.

3. An attachment according to claim 2, wherein said rigidly-secured ball, said flange, and said socket-shaped part are made in one piece.

4. An attachment according to claim 2, wherein said shock-absorber device comprises a threaded shank, a spring and a nut engaged on said shank, and a coupling element secured to said body, serving as a support for said spring and keeping said device within said socket-shaped part.

5. An attachment according to claim 1, wherein said balls are substantially spherical in shape and equal in diameter.

6. An attachment according to claim 5, wherein said rigidly-secured ball comprises a flat facing said other ball.

7. An attachment according to claim 1, wherein said slide comprises a straight, profiled groove intended for engagement of said balls and a flat support surface serving for guidance of a front face of said body.

8. An attachment according to claim 7, wherein said profile of said groove comprises an arcuate portion with an angular span of more than 180° and a slot having two faces parallel to one another, and wherein said flat support surface is parallel to the longitudinal axis of said groove, said groove opening out into said flat support surface.

9. An attachment according to claim 2, wherein said slide comprises two edges parallel to each other and to said groove and projecting from said flat support surface.

10. An attachment according to claim 9, wherein said flange is fitted in width to the space between said edges.

* * * * *